Feb. 9, 1954 P. K. FUJIHARA Plant Pat. 1,250
GRAPEVINE
Filed July 27, 1953
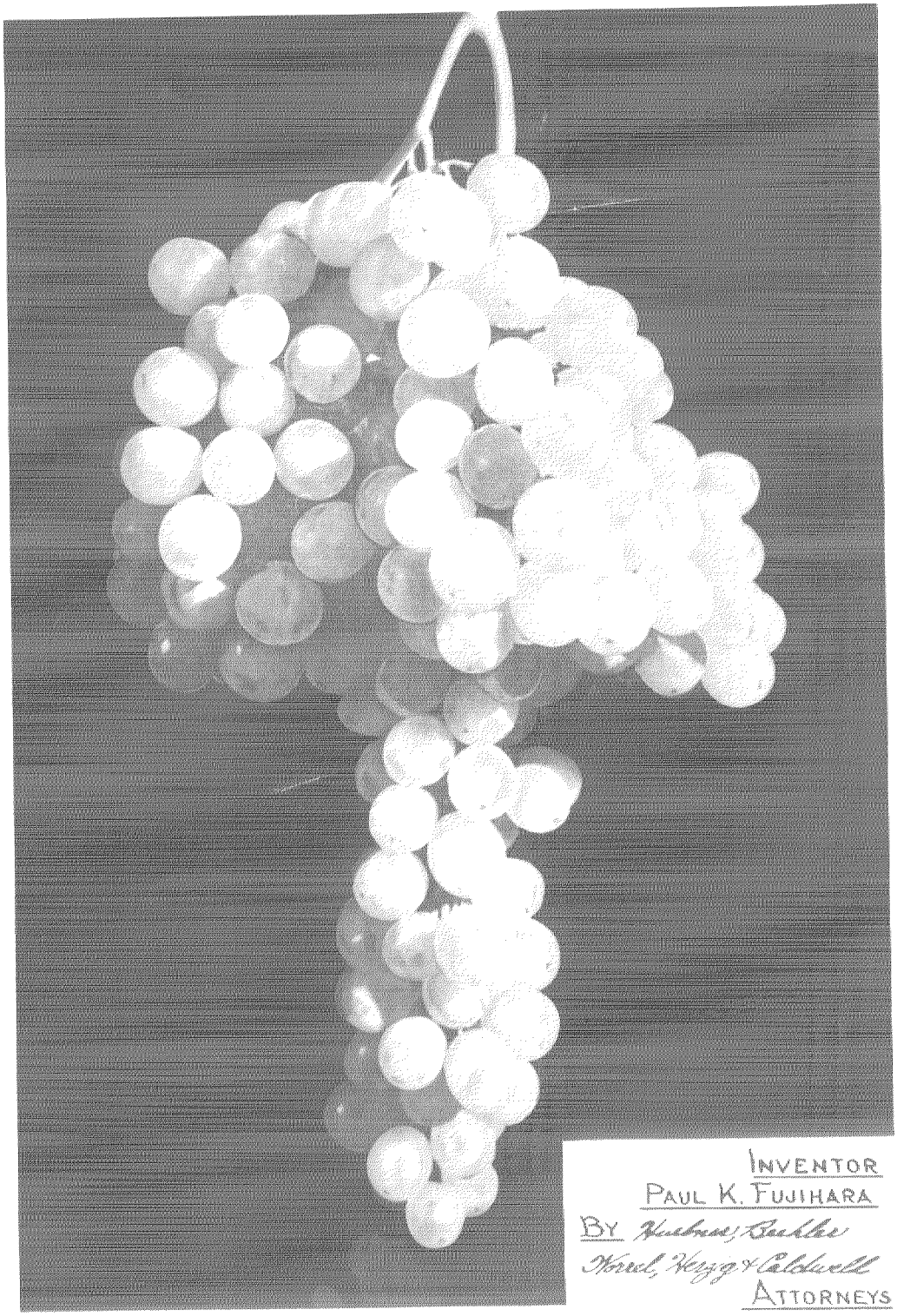
INVENTOR
PAUL K. FUJIHARA
BY Hubbard, Geckler
Hood, Heyza & Caldwell
ATTORNEYS Patented Feb. 9, 1954

Plant Pat. 1,250

UNITED STATES PATENT OFFICE 1,250

GRAPEVINE

Paul K. Fujihara, Del Rey, Calif.

Application July 27, 1953, Serial No. 370,659

1 Claim. (Cl. 47—62)

The present invention relates to a plant invention or discovery and more particularly to a new and improved variety of grape vine. The present invention generally belongs to the so-called white table grape class of grapes characterized by the Gordo blanco of Australia, Muscat of Jerusalem, Moscatel Gordo blanco of Spain, White Hanepoot of South Africa, Muscat d'Alexandria of France, Zibibbu and Gerosolimitana bianca of Sicily and the White Malaga. The Muscat of Alexandria is one of the finest and most valuable grapes in that it is an excellent table grape, a good shipper, produces excellent raisins, and is popular for wine making. It is grown in almost all viticultural regions where the climate is suitable. It requires considerable heat to produce grapes of perfect maturity and thus is popular in North Africa, South Africa, Australia, California, Spain, Italy, Southern France, Sicily, and regions of comparable climate.

The Muscat of Alexandria however possesses certain disadvantages which the present invention is believed to overcome. It is characterized by fruit widely varied in size and speed of reaching maturity, it not being unusual to find immature berries as well as raisins in the same bunch, as well as berries of widely varied sizes. Further, the bunches produced by the Muscat of Alexandria vary greatly in that bunches having overly crowded berries and straggly bunches are frequently found on the same vine. As previously mentioned, raisins made from muscats are popular but unfortunately are somewhat difficult to produce. The grapes require long periods of hot weather to mature and thus are not ready for drying until late in the season. Thus, early rains frequently destroy entire crops of muscat grapes laid in the sun to dry. Further, such grapes reach maturity concurrently with a vast number of other white table grape varieties and thus experience extensive competition in sale as a table grape. It is excellently suited to wine production but because of its heavy flavor its use is limited to a narrow class of wines.

It has been observed that the Red Malaga (Molinera Castiza) has relatively few of the muscat disadvantages in that it ripens early, grows rapidly, and produces bunches of grapes of greater uniformity. This grape however possesses certain disadvantages that are not characteristic of the muscat. It does not make good raisins, possessing a relatively low sugar content. It is undesirable in wines because of insufficient sugar and acid content. Although relatively successful as a table grape, its relatively low sugar content and the fact that it is a red grape ripening at a time when other red grapes are available substantially reduces its commercial value.

The grape varieties specified herein as the parents of the new variety and the others designated for descriptive convenience are all unpatented grapes that have been well-known for many years.

These and other difficulties have motivated a quest by the present inventor, covering many years of work with grape vines, having the following objectives:

To provide a grape vine having improved growth characteristics and productive of excellent grapes at a season of the year conducive to ready sale as table grapes, early enough for drying purposes, and suitable for wine making purposes.

To provide a grape vine productive of berries of the so-called white grape type that ripen much earlier than other so-called white grapes.

To provide a grape vine having the desirable attributes of the Muscat of Alexandria and Red Malaga (Molinera Castiza).

To provide a hybrid of the Muscat of Alexandria and the Red Malaga (Molinera Castiza) that possesses the rapid, vigorous growth of the malaga; that ripens at about the time of said malaga; that bears greenish yellow to light amber berries characteristic of said muscat; which berries are of substantially uniform size, color, shape, and ripening speed, and of the general malaga flavor, but which possess the heavy sugar content of the muscat, and which ship well, make excellent raisins, and are suitable for wine.

To provide a superior grape of the so-called white grape type that is an excellent table grape in its uniform and attractive appearance, its sweet pleasant taste, and its excellent keeping qualities.

To provide a grape of the general muscat type which ripens sufficiently early in the season to avoid the losses incident to early fall rains normally experienced in making muscat raisins.

It is submitted that these and other objectives apparent in the following description have been achieved by the new variety grape vine of the present application.

The drawing of this application consists of a tinted photograph of a bunch of grapes of the new variety.

The origin of the new variety grape is a seedling resulting from the cross-pollination by the applicant of a Muscat of Alexandria and a Red Malaga (Molinera Castiza). Extensive cross-pollination of these two grape varieties was conducted, seedlings thereof cultivated and the present variety resulted from careful selection of the seedlings and the asexual reproduction thereof by cuttings, all in a vineyard cultivated and controlled by the applicant adjacent to the city of Del Rey, county of Fresno, State of California.

The vine of this new improved grape is about the size of the Red Malaga (Molinera Castiza) and thrives best under similar growing conditions and when pruned and trained as the Red Malaga (Molinera Castiza), rather than as the muscat. The trunk of the vine is stocky, in this respect similar to the Red Malaga (Molinera Castiza), and not as stocky as the muscat. The growth of the vine is much more rapid and vigorous than the muscat, its canes growing to approximately five times the length of the muscat. The canes are thicker and much longer than the Muscat of Alexandria but possess the characteristic brown coloring of said muscat. The nodes are spaced closer near the base of the canes with the distances between the nodes much greater than the muscat at all points on the cane. Other than in color, the canes are similar to the Red Malaga (Molinera Castiza). The spacing of the nodes may also be likened to the spacing of the nodes of the canes of the Fresno Cardinal grape. The canes are somewhat less pithy than the muscat. The tendrils are intermittent, long, and frequently bifid. The young shoots are green and slightly maroon tinted and covered with flocculate tomentum prior to maturity. The buds are prominent, partly pubescent, pointed, and much larger than the muscat, being in this particular similar to the Red Malaga (Molinera Castiza).

The leaves are five lobed, the upper sinuses being deep and frequently closed, the lower sinuses usually well marked and open. The lower or petiolar sinuses are usually wide open at maturity but in some instances are entirely nonexistent. The leaves are medium in size, being smaller than the leaves of its malaga parent and about the size of its muscat parent, about as broad as long, and substantially glaborous on both surfaces. The leaves are usually circumscribed by outwardly extended teeth which vary from numerous and well defined to almost nonexistent. Generally the teeth are fewer in number than on leaves of the Muscat of Alexandria and are shorter than the teeth on the leaves of the Red Malaga (Molinera Castiza). In coloring the leaves are similar to the leaves of its muscat parent.

The petioles of the improved grape vine are frequently light red to crimson, usually very long, sometimes thick and glaborous. The petioles are readily distinguished in color from the purpose red of the muscat and the light green of the Red Malaga (Molinera Castiza).

The bunches of berries produced by the improved grape vine are large, long, shouldered, and slightly branchy. The peduncle is fairly thick, usually thicker than the muscat peduncle, and of medium length. The berries are large, and substantially spherical. As is readily apparent in the drawing, the berries are of almost identical form, size, color, and are characterized by almost perfect uniformity in degree of maturity. These uniform characteristics have obvious marketing advantages and are considered of particular significance. The skin is fairly thin yet the berries are firm and ship well. In this respect this grape is a good deal like the Thompson Seedless berries. At maturity the berries range in color from clear dull green-yellow, Plate XVII, to barium yellow, Plate XVI, as referred to in Ridgway's Color Standards and Color Nomenclature, 1912, and may be permitted to hang on the vines for a considerable period after ripening. In this particular they are somewhat similar to berries of the Muscat of Alexandria and directly contrast with the berries of the Red Malaga (Molinera Castiza) which must be picked promptly upon reaching maturity. The berries possess a thin white bloom at maturity. "Shot" berries are almost entirely unknown in this new variety.

Although the improved grape is similar to the Thompson Seedless variety, in the particulars set forth above, it is readily distinguishable therefrom in that its berries contain one or two seeds as compared with no seeds for the Thompson. The berries are normally three to four times as large as the berries of the Thompson and the bunches wider and longer. The bunches are found at almost every cane joint and the crop heavier than that of the Thompson, requiring heavy thinning. The berries are generally more spherical than the berries of the Thompson grape and the flavor more closely akin to that of a Muscat than that of the Thompson. The berries ripen from ten days to two weeks earlier than the Thompson, although the buds are formed in the spring approximately ten days later than those of the Thompson. The canes of the improved grape vine are somewhat browner than the canes of the Thompson and have a substantially less yellow tinge thereto than the Thompson. The canes are somewhat more closely jointed and not quite as vigorous in growth as the Thompson canes, in this particular being more like the Muscat of Alexandria.

The berries are excellent for table grapes possessing the outstanding appearance described above and apparent in the drawing. Their flavor is somewhat similar to that of the Red Malaga (Molinera Castiza) but much sweeter, in sugar content closely approaching the Muscat of Alexandria. The berries are generally firmer than the muscat and ship much better as a table grape than the muscat and the Red Malaga (Molinera Castiza). The firmness of the berries and the superior shipping characteristics of the subject grape are clearly distinguished from each of its parents, in these particulars being somewhat similar or superior to that of the Thompson Seedless grape, ten days to two weeks earlier than which it ripens. Inasmuch as the berries of the subject grape can be permitted to hang on the vines for a considerable period after ripening and inasmuch as they mature only ten days to two weeks earlier than the Thompson Seedless grapes, their harvesting seasons under similar growing conditions frequently overlap for brief periods. The berries make excellent raisins, closely approaching the muscat in quality and sugar content. In this ability, and in its ability to make quality wine, the improved variety is far superior to the Red Malaga (Molinera Castiza).

The peduncles are slender, long, and only slightly warted. Not only do the berries of the bunches mature uniformly, but the berries ripen approximately four weeks earlier than berries of its parent, the Muscat of Alexandria which possesses a similar color. The ripening usually occurs approximately two to three weeks in advance of the ripening of the other parent, the Red Malaga (Molinera Castiza), whose berries are red in color. The berries of the present improved variety are ready for shipment to market as table grapes approximately six weeks prior to white malagas and four weeks or more prior to the Muscat of Alexandria. Obviously the time of ripening varies according to the climate and the weather experienced during the season of maturation, but generally may be said to occur near the end of July in areas having climates similar to that of the San Joaquin Valley, California.

The improved variety tends to bear excessive quantities of grapes. In this respect, it is distinguishable from both of its parents. It tends to bear bunches of grapes at each node on each cane. Best results are attained when the variety of the present invention is pruned in the manner normally employed for the Red Malaga (Molinera Castiza), and as soon as the berries have set, the bunches are preferably thinned so that each cane bears only one bunch, or at most no more than two.

The present variety is appropriately characterized by its vigorous growing habits, by its excessively heavy crops when unthinned, and by its large, long, shouldered slightly branching bunches of substantially spherical, greenish yellow to light amber berries. The berries are even more particularly characterized by their uniformity in size, color, shape, and speed of maturation and by their ripening approximately thirty days earlier than the Muscat of Alexandria at a time when no other grape of its color is available for market.

Not only is the present variety vigorous in its growing habits but apparently is resistant to Pierce's desease, also known as Anaheim disease, California vine disease, mysterious vine disease and vine plague. Although the present variety has never been subject to Pierce's disease, it of course can not yet be definitely established that it will not subsequently contract the disease.

Having clearly described the new and improved grape vine, what I claim is:

The variety of grape vine herein described and illustrated characterized by its vigorous growing habits; by excessively heavy crops when unthinned; and by large, long, shouldered, slightly branching bunches of substantially spherical, clear dull green-yellow to barium yellow berries containing seeds which are particularly characterized by uniformity in size, color, shape, and speed of maturation within their respective bunches and by early ripening for grapes of such size and color; said berries maturing approximately thirty days earlier than the Muscat of Alexandria, its parent vine having somewhat the same colored berries, and about two and one half weeks earlier than its other parent the Red Malaga (Molinera Castiza) having red berries, under similar growing conditions.

PAUL K. FUJIHARA.

No references cited.